United States Patent [19]

Poley

[11] Patent Number: 5,176,686

[45] Date of Patent: Jan. 5, 1993

[54] APPARATUS FOR PACKAGING, FOLDING, RIGIDIFYING AND INSERTING AN INTRAOCULAR LENS

[76] Inventor: Brooks J. Poley, 1820 Medical Arts Bldg., Minneapolis, Minn. 55402

[21] Appl. No.: 688,722

[22] Filed: Apr. 19, 1991

Related U.S. Application Data

[60] Continuation-in-part of Ser. No. 628,207, Dec. 14, 1990, abandoned, which is a division of Ser. No. 416,361, Oct. 3, 1989, Pat. No. 4,988,352.

[51] Int. Cl.⁵ .............................................. A61F 9/00
[52] U.S. Cl. ...................................... 606/107; 606/1; 623/4; 623/6
[58] Field of Search ................................ 606/20-26, 606/107, 1; 623/4, 6

[56] References Cited

U.S. PATENT DOCUMENTS

| | | | |
|---|---|---|---|
| 3,259,131 | 7/1966 | Kanbar et al. | 606/25 |
| 3,266,492 | 8/1966 | Steinberg | 606/23 |
| 3,393,679 | 7/1968 | Crump et al. | 606/26 |
| 3,575,176 | 4/1971 | Crump et al. | 606/25 |
| 3,618,610 | 11/1971 | Hannant | 606/25 |
| 3,913,581 | 10/1975 | Ritson et al. | 606/23 |
| 4,451,938 | 6/1984 | Kelman | |
| 4,573,998 | 3/1986 | Mazzocco | |
| 4,605,409 | 8/1986 | Kelman | |
| 4,615,703 | 10/1986 | Callahan et al. | 606/107 |
| 4,619,657 | 10/1986 | Keates et al. | 606/107 |
| 4,636,210 | 1/1987 | Hoffer | |
| 4,681,102 | 7/1987 | Bartell | 128/303 |
| 4,702,244 | 10/1987 | Mazzocco | |
| 4,747,404 | 5/1988 | Jampel et al. | 606/107 |
| 4,763,650 | 8/1988 | Hauser | 606/107 |
| 4,769,034 | 9/1988 | Poley | 623/6 |
| 4,785,810 | 11/1988 | Baccala et al. | 606/107 |
| 4,819,631 | 4/1989 | Poley | 606/107 |
| 4,832,022 | 5/1989 | Tjulkov et al. | 606/22 |
| 4,836,201 | 6/1989 | Patton et al. | 606/107 |
| 4,906,247 | 3/1990 | Fritch | 606/107 |
| 4,911,158 | 3/1990 | Weatherly | 606/107 |
| 4,934,363 | 6/1990 | Smith et al. | 606/107 |
| 4,955,889 | 9/1990 | Van Gent | 606/107 |
| 4,976,716 | 12/1990 | Cumming | 606/107 |

FOREIGN PATENT DOCUMENTS 0402138  12/1990  European Pat. Off. ............. 623/6

OTHER PUBLICATIONS

"Soft IOL Technology: the New Frontier" by Virginia L. Bohn Ocular Surgery News, vol. 5, No. 5, Mar. 1, 1987.
"Pathologic Findings of an Explanted Silicone Intraocular Lens" Newman, J Cataract Refract Surg-vol. 12, May 1986.
"Implantation Procedure" by Charles H. Bechert, M.D., Precision-Cosmet Co., Inc.
"Second Generation IOL"-Allergan Medical Optics.
"Frigitronics CE-82" An Advanced Ophthalmic Cryosurgical System.

Primary Examiner—Stephen C. Pellegrino
Assistant Examiner—Glenn K. Dawson
Attorney, Agent, or Firm—Wood, Herron & Evans

[57] ABSTRACT

Apparatus for folding an intraocular lens about a blade-like inserter to reduce its width, and then rigidifying the folded lens in situ by chilling it until it remains folded on the inserter for insertion into the eye. The lens is positioned for folding on a seat in the folding apparatus, and the inserter blade is placed on the lens. A hinged arm folds one half of the lens over the blade. The lens is then chilled until rigid so that it remains folded around the blade, as by a cryogenic fluid circulated through the inserter. Also disclosed is a lens package having a removable carrier by which the lens can easily be removed from the package and positioned in the folding apparatus, without loss of sterility.

35 Claims, 4 Drawing Sheets

APPARATUS FOR PACKAGING, FOLDING, RIGIDIFYING AND INSERTING AN INTRAOCULAR LENS

RELATED APPLICATIONS

This application is a continuation-in-part of my copending application Ser. No. 628,207, filed Dec. 14, 1990, titled "Apparatus for Implanting a Frozen Intraocular Lens", now abandoned which was in turn a division of my Ser. No. 416,361, filed Oct. 3, 1989, now U.S. Pat. No. 4,988,352, issued Jan. 29, 1991, titled "Method and Apparatus For Folding, Freezing and Implanting Intraocular Lens."

FIELD OF THE INVENTION

This invention relates generally to the implanting of intraocular lenses to replace the natural lens of the eye. More specifically, it relates to apparatus for folding a lens about a blade-like inserter while maintaining sterility, and for cooling the lens to a state of rigidity while folded around the inserter, for insertion into the eye. Other aspects of the invention relate to a package or carrier for the lens to be folded, and to the inserter.

BACKGROUND

The use of intraocular lenses ("IOLs") has been highly developed in recent years, especially for implantation after the removal of a cataract, and such operations are now common medical procedures. In such procedures it is desirable to minimize the size of the incision which must be made to insert and position the IOL in the eye, in order to shorten the time required for the eye to heal and to minimize any chance of failure. Most implanting techniques have required that the incision in the eye be slightly wider than the diameter of the IOL to be implanted so that the lens can be inserted through the incision. Recently techniques have been developed for reducing the width of a lens by folding it prior to insertion. The use of a folded lens enables a smaller incision to be used than otherwise would be required. For example, a lens of 6.0 mm diameter can, if folded, be inserted through an incision only about 3.2 mm wide.

My U.S. Pat. No. 4,769,034 discloses a foldable resilient lens which is retained in a folded configuration, by a retainer which is wrapped around the lens and temporarily held in place by severable ties around the folded lens. This enables the lens to be inserted through the same small incision which is used to remove a cataract from the eye. Once inserted in the eye the retainer is released and removed, and the lens resiliently unfolds to its normal configuration. My U.S. Pat. No. 4,911,914 discloses another type of retainer for holding a lens folded during insertion, in which the retainer is integral with the lens itself. Sutures which extend through apertures in overlying parts of the folded lens are also disclosed.

My U.S. Pat. No. 4,819,631 discloses apparatus for folding a lens for insertion. That apparatus presents a lens seat on which the lens is placed. A base has a guide for aligning an inserter so that the blade of the inserter is properly positioned on the lens. A hinged or swingable folding arm folds one half of the lens around the blade. Preferably the inserter blade has a teardrop-shaped cross section which closely conforms to the space between the leaves of the folded lens so that the lens surface closely engages the blade.

The techniques referred to above are relatively complicated in that they require securing a retainer around or suturing the folded lens, or forming a retainer integrally with the lens. My U.S. Pat. No. 4,988,352 discloses an intraocular lens which is retained in the folded configuration by chilling it until it becomes inflexible and looses its tendency to unfold. A cryogenic gas is applied to rigidify the lens. The chilling (which can be thought of as "freezing" even though no liquid/solid phase change occurs) obviates the need for a surrounding or attached retaining means to hold the lens in the folded configuration. This facilitates the surgical procedure and enables a smaller incision to be used. The rigidified folded lens is inserted into the eye and there warms so that it returns to its original flexible, unfolded configuration. The lens may be rigidified on an inserter or blade for positioning it within the eye.

BRIEF DESCRIPTION OF THE INVENTION

This invention is directed to an improved apparatus for folding a lens around an inserter and cooling it to rigidity on the inserter. The improved folding apparatus facilitates the positioning of the lens in the folder; facilitates maintenance of sterile conditions during the positioning and folding of the lens; and accommodates the folding and chilling of lenses of a range of different shapes, diameters, thicknesses, optical strengths and materials.

The invention is also directed to an improved form of inserter for folded, rigidified lenses.

As disclosed in my U.S. Pat. No. 4,988,352, previously referred to, I have found that it is desirable to rigidify a folded lens from the "inside out" by cooling it from a chilled blade between its folded leaves, rather than from the "outside in." The heat transfer rate of lens plastic materials is relatively poor, and if rapid (cryogenic) cooling is applied through a blade between them, the surfaces of the lens which are in contact with the blade will cool more rapidly than the surfaces of the lens which are away from the blade. In this manner the blade-engaging surfaces of the lens rigidify while the outer surfaces (which contact eye tissue first during insertion) remain somewhat warmer. This minimizes the danger of freezing eye tissue with which the lens may come in contact. Once the lens is rigidified on the inserter and the inserter is removed from the folding apparatus, cooling can be applied thereafter through the inserter to maintain the lens rigid until such time as it is desired to permit it to unfold within the eye. This invention provides apparatus for so chilling the lens.

Intraocular lenses are supplied commercially in a variety of different contours and configurations. The peripheral shape of the lens may be oval or circular; and the positions and shapes of the haptics may vary from model to model. Moreover, apart from differences in the shapes of the lenses, lens thicknesses varies with power; and lenses of different materials may be of different thicknesses, even for the same strength. It is desirable that the folding apparatus bring the lens, whatever its shape, into close contact with the inserter blade. In order to do so the configuration of the lens folding area should accommodate the precise shape and size of the specific lens. From the manufacturer's standpoint it is desirable to provide a folding apparatus which can accommodate a variety of different lenses, which the present invention does.

The preferred folding and chilling apparatus of this invention includes a base having a seat for supporting a first face of the lens, means for holding the lens in place for folding, an aligning guide for positioning an inserter so that a blade portion of the inserter is positioned on about one-half of the concave (rear) face of the lens, and an arm movable with respect to the seat for folding the other half of the lens around the inserter blade. The seat is presented in a cavity in the base and engages half the lens, which it holds in a horizontal position. The swing arm is movable about an axis parallel to, and preferably colinear with, the line about which the lens is to be folded. The inserter has a thin blade or fin approximating the inside width of the folded lens. A projecting tip of the inserter is receivable in a tip socket on the folder which holds the blade in proper position while the lens is being folded.

In order to accommodate lenses of different sizes, shapes and thicknesses, the lens is received in the folder apparatus on a seat which is preferably provided by a carrier that is removable from the base. Carriers with seat adapters for different lens configurations can be placed in the base to accommodate different sizes and designs of lenses. For this purpose the seat is preferably formed in a removable lens carrier which is positionable in the base. The seat is configured to engage and support about one-half the width of the lens: the folding arm engages that half of the lens which is not carried on, and which projects off, the seat. The removable carrier may include a recess for receiving haptics which project from the lens. The carrier can have a handle by which it can be moved to and from the base; and the carrier itself may be used for packaging and shipping the lens, being positionable in a surrounding protective package or frame. The frame, with the lens on an adapter seat in the carrier and seated within the frame, is overwrapped or otherwise sealed so that lens sterility can be maintained during shipment until at the time of folding. At that time the protection is removed, the carrier containing the lens is removed from the frame (which does not require manual contact with the lens), and is seated in the folding apparatus. The lens can thus be packaged, transported, unwrapped, seated in the folding apparatus, folded and rigidified for insertion in the eye, without being touched by the human hand.

DESCRIPTION OF THE DRAWINGS

The invention can best be described by reference to the drawings, in which.

DETAILED DESCRIPTION

Figure 1:
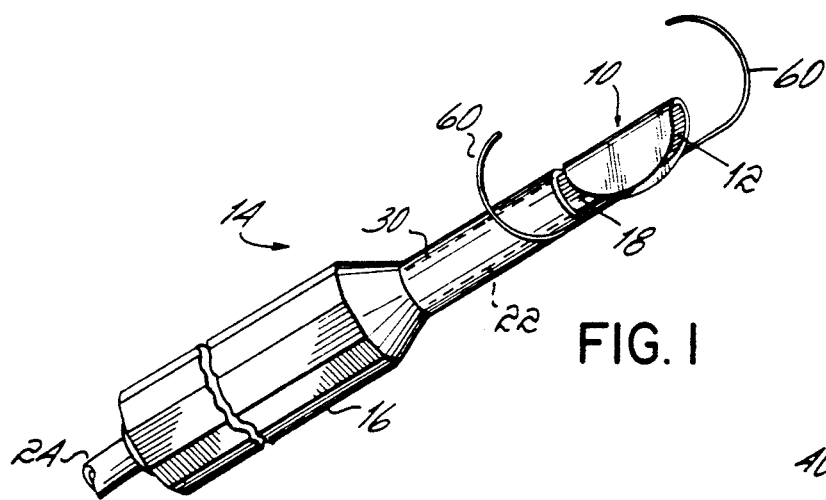
FIG. 1 is a perspective view of a first embodiment of an inserter having a lens folded and rigidified around a blade, ready for insertion into an eye.

FIG. 1 of the drawings shows a lens 10 which is folded around the "blade" 12 of an inserter or tool 14. Lens 10 may be any of a variety of resiliently foldable intraocular lenses known per se, for example, the resilient acrylic lens made by Ioptics, Inc., or the silicone lens made by American Medical Optics, Inc. Inserter 14 may of the type generally described in my previously identified U.S. Pat. No. 4,988,352. It serves to position the lens for folding; to assist in cooling the lens; to carry the folded lens to the incision in the eye; to insert the folded lens through the incision; to assist in warming the lens so that it again becomes flexible and unfolds within the eye at a desired time and position; and/or to position and manipulate the lens within the eye. The form of inserter shown in FIG. 1 has a handle 16 which mounts the blade 12 about which the lens is folded. In cross-section, blade 12 is shaped like a teardrop or airfoil, corresponding to the cross-sectional shape of the region between the opposed leaves or halves of the lens when folded (see FIG. 4). The blade has opposite faces 18 and 20, of width approximating the radius or half-width of lens 10 for engaging the respective leaves of the folded lens. Blade 12 is preferably metal for heat transfer purposes, and has a shank 22 which extends into and is seated in insulating handle 16 of the inserter (see FIG. 2). The shank preferably has internal heat exchange means such as fins 23 by which it can be cooled and, through the shank, the blade itself. A coolant line 24, which may be a flexible insulated conduit, connects an external coolant source 26 with inserter 14, to remove heat from the blade. Line 24 may include a return line and a control valve 28 for regulating the rate of flow of cryogenic fluid, and hence the temperature of the blade and that of lens 10. In order to minimize contact of the cold blade with eye tissue, exposed portions of the blade 12 not covered by the lens may be insulated with a non-stick plastic coating or sleeve 30.

From the foregoing it can be seen that the freezer/inserter can rigidify the lens by cooling it through the blade. By controlling the rate of coolant flow to the blade, the lens can be rigidified, or maintained rigid, in air and in the eye, and its unfolding can be regulated by warming to provide unfolding at the desired time and rate. Frigitronics Corporation produces and sells a "Frigitronic Ophthalmic Cryo Surgical Device," Model CE-82, which has heretofore been used to remove cataracts, freeze retinal areas, and to destroy ocular tissue such as the iris and cornea by freezing it in the eye. As sold, that device has a round, rod-like freezing tip having a shank which is seated in a handle. The shank is cooled by a gas circulating within it, typically nitrous oxide (N₂O) from an external source. By controlling the rate of gas flow, the temperature of its tip can be set at a desired temperature from room temperature down to about −90° C., and for that purpose the gas flow controller can be calibrated in degrees. As sold, that device is not suitable to fold or rigidify an IOL in accordance with this invention, but it is illustrative of one type of hand holdable, controllable cooling means which can be modified with a blade about which a lens can be folded as described herein. So modified, the lens can be rigidified or frozen by heat removal from its surfaces on each side of the blade, and can then be carried on the blade and inserted.

With the inserter 14 the lens can be cooled to become rigid but with its outside faces relatively warmer than its inside faces. A lens so chilled does not subject eye tissue to the actual temperature of its inside faces, and does not stick or adhere to the incision or internal eye tissue. The nature of the coolant for freezing the lens is not critical. A cryogenic fluid such as gas evaporated from liquid N₂O, N₂, or O₂, or CO₂ from dry ice can be used, by way of example. An acrylic lens immersed in liquid nitrogen will rigidify within a few seconds; use of cryogenic N₂O gas requires somewhat longer. The lens should be rigidified at as high a temperature as will hold it folded for implanting, so as to minimize any chance of damage to eye tissue by freezing.

Figure 2:
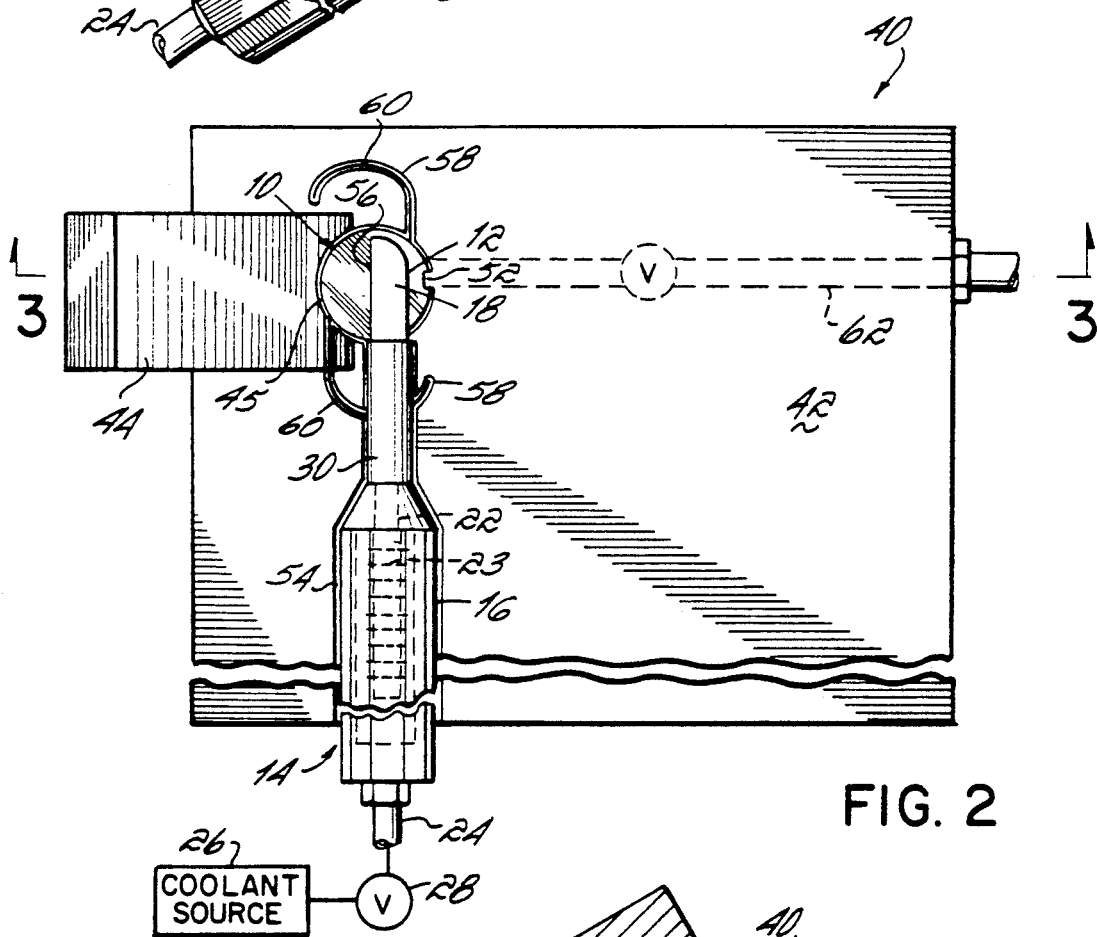
FIG. 2 is a top plan view, partly diagrammatic in nature, of one form of folding apparatus in accordance with the invention, showing the blade of the inserter of FIG. 1 positioned on a lens, prior to folding.
Figure 3:
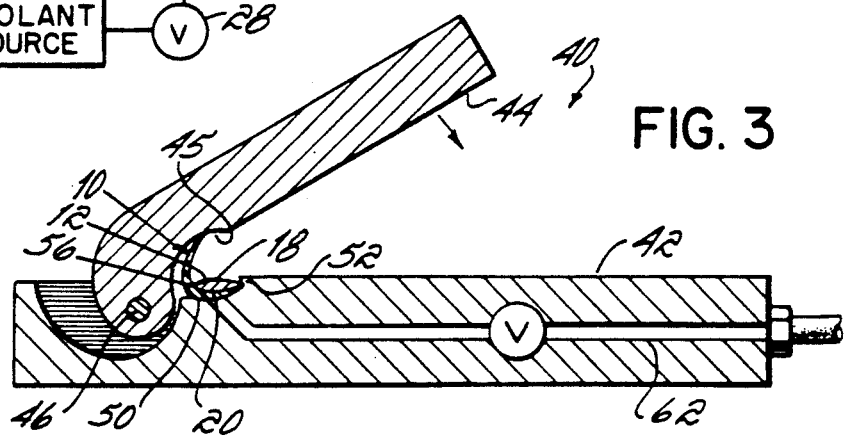
FIG. 3 is a vertical section taken on line 3—3 of FIG. 2, showing the swing arm folding the lens about the inserter blade.
Figure 4:
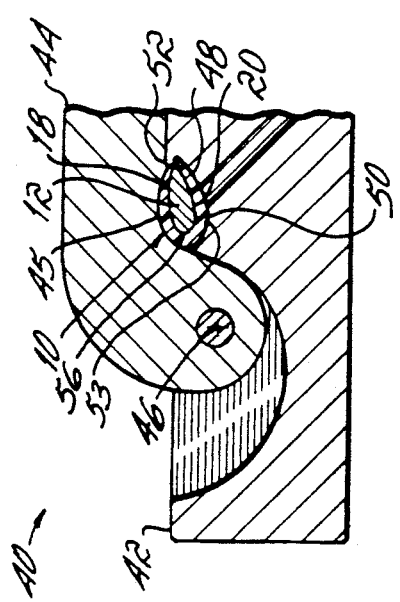
FIG. 4 is an enlarged cross-section similar to FIG. 3 but showing the lens folded around the inserter in the apparatus.

The folding apparatus of the invention greatly facilitates folding the lens around the inserter blade which, if done manually (as with a tweezers), would be awkward at best. A related type of lens folding apparatus as described in my previously identified U.S. Pat. No. 4,819,631. However, that patent does not disclose either folding the lens on an inserter or rigidifying the lens by chilling it. The first embodiment of folding and freezing apparatus 40 which is shown in FIGS. 2-4, includes a base 42 and a swingable arm 44 which is hinged to the base for rotation about an axis 46. Axis 46 is parallel to but laterally offset from the edge 56 of the blade about which the lens folds (FIG. 4). The base 42 has a recess or cavity 48 which presents an upwardly facing seat 50 for engaging and supporting part of one lens face 53 (the convex lens face) placed downward on it. Seat 50 is configured so that approximately one-half the width of the unfolded lens will rest on it; the remaining width of the lens projects off seat 50, for engagement by arm 44 (see FIG. 2). An abutment or lip 52 is useful to hold the lens on seat 50 so that lens alignment is maintained during folding.

Inserter positioning means which may be in the form of a recess or socket 54 is provided in base 42 to receive and position the handle 16 of the inserter, so that blade 12 is properly aligned on the lens over seat 50. The recess positions the lens-folding edge 56 of blade 12 parallel to hinge axis 46 (FIG. 3). Seat 50 includes one or more grooves or recesses 58 to receive the haptics 60 of the lens (FIG. 2). The handle 16 and base 42 surfaces which contact the lens should be nonadherent to the lens when chilled.

Arm 44 can be folded over the lens (clockwise as seen in the drawings), to engage, lift and fold one-half of the lens over the top of the blade so that the blade is sandwiched between the opposed halves or leaves of the lens. The arm presents a seat portion 45 which engages the portion of the lens that projects off base seat 50 for folding.

Once folded, the lens is made rigid by cooling the inserter blade. If the inserter has inadequate cooling capacity, the folding apparatus may be provided with a coolant passage 62 which opens to or communicates with seat 50 to assist in chilling the blade and removing heat from the upper (outside) lens surface. Passage 62 is connected to a source of cryogenic (chilling) gas or liquid such as source 26. After the lens has been sufficiently chilled, arm 44 is swung open and the inserter is removed, with the cold rigid lens on the blade. Cooling can be supplied to the inserter handle thereafter to slow the otherwise rapid rate of warming in air.

Figure 5:
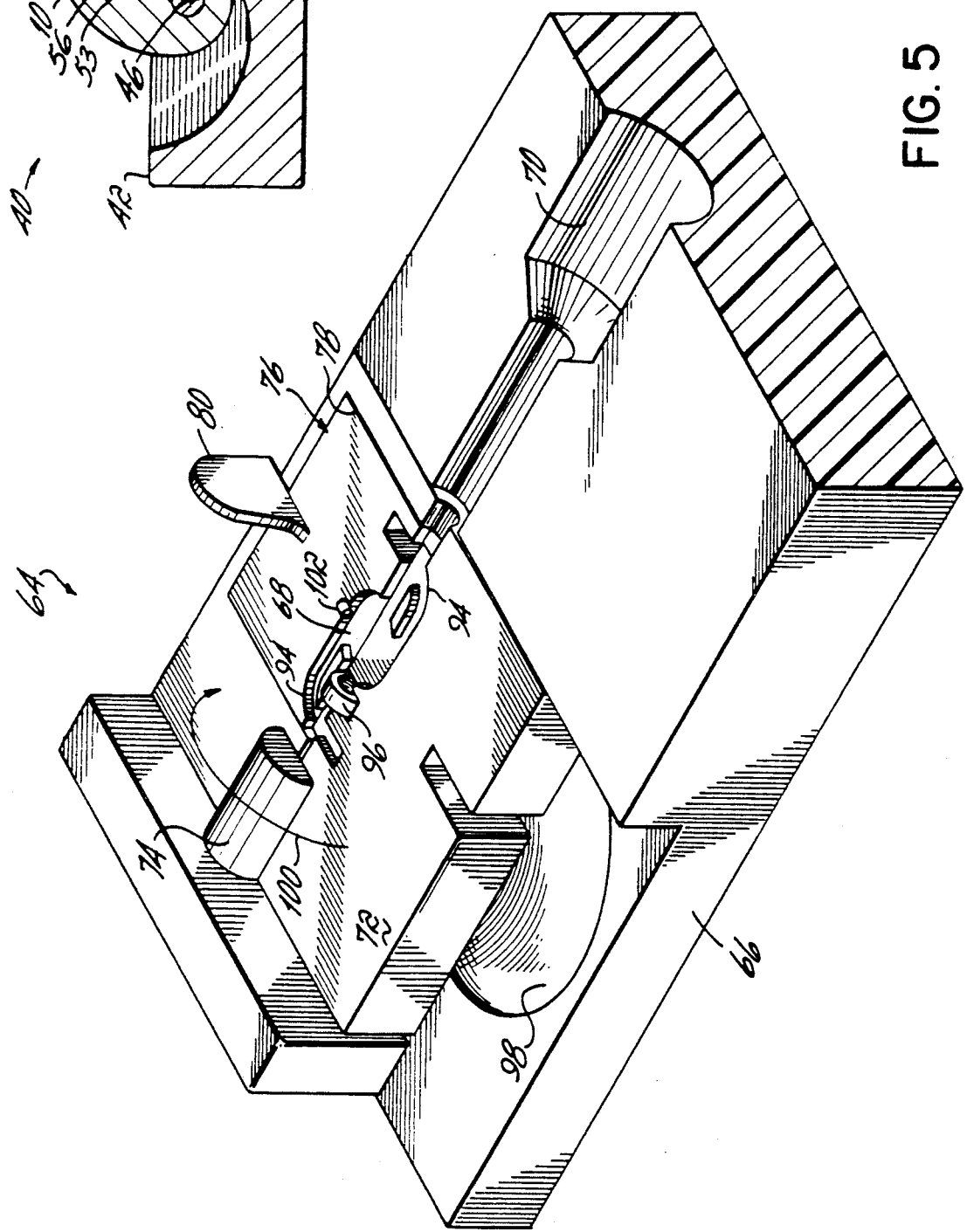
FIG. 5 is a perspective view of a preferred form of folding apparatus in accordance with the invention, into which the lens can be placed while it remains in a separate carrier.

FIG. 5 shows the embodiment of folding apparatus 64 which is presently preferred. This apparatus differs from that described above in connection with FIGS. 2-4, in that it accepts different seats for different lenses, and in that the lens seat is provided on a removable lens carrier or adaptor 76. The apparatus includes a base 66, means presenting a seat 68, a positioning guide 70 for receiving and holding the handle of an inserter, and a movable arm 72 having a pivot 74 for swinging movement to fold the lens leaf over the blade. However, unlike the first disclosed embodiment, in this embodiment the seat 68 is presented on a separate lens carrier 76 which is removable from a socket or aperture 78 in base 66. Carrier 76 has a handle or grip 80 by which it can be brought to and lifted from the socket 78 of the folding apparatus, while a lens is seated on carrier seat 68. It should also be noted that the pivot 74 for arm 72 is preferably on one side of seat 68, rather than below it as in the first embodiment, so as to be colinear with the blade edge about which the lens folds.

Figure 10:
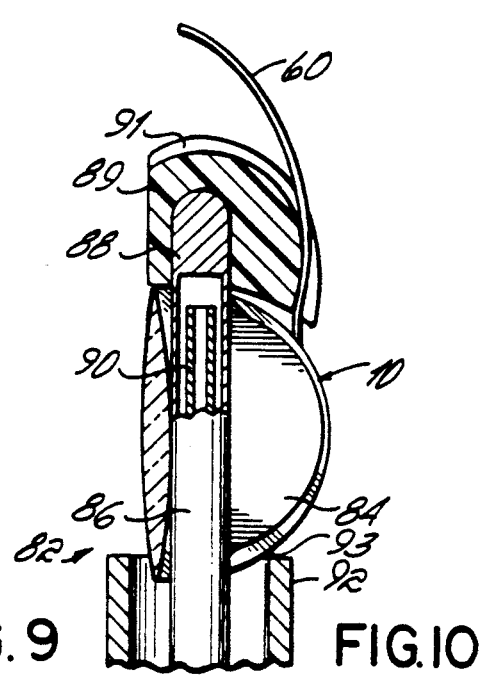
FIG. 10 is an enlarged axial cross-sectional view of the tip portion of the inserter of FIG. 8, showing the sleeve abutting the blade for insertion.

A preferred form of inserter 82 for use with the apparatus of FIG. 5 is shown in FIGS. 8-11. This inserter 82 has a blade in the form of a semi-circular fin 84 which is attached along a diametral edge to a tube 86. As shown in FIG. 10, tube 86 is closed at its outer end 88 and has an axial inner tube 90 within it. Cryogenic fluid is supplied from a source such as source 26, into the inner tube 90, exits from that tube adjacent the outer end 88 of outer tube 86, and then flows reversely between inner tube 90 and outer tube 86, thereby removing the heat of the lens where the lens engages tube 86 and fin 84. This heat transfer arrangement is more efficient than that of the embodiment of FIG. 2. The inserter has a rounded tip 89 which projects axially beyond blade 84 and tube end 88, and which is useful to help hold and align the blade during folding. Tip 89 fits into an opening in the alignment guide 96 (FIG. 5) to position blade 12 correctly on the lens. Tip 89 is made of an insulating material so that it does not chill ocular tissues.

Figure 11:
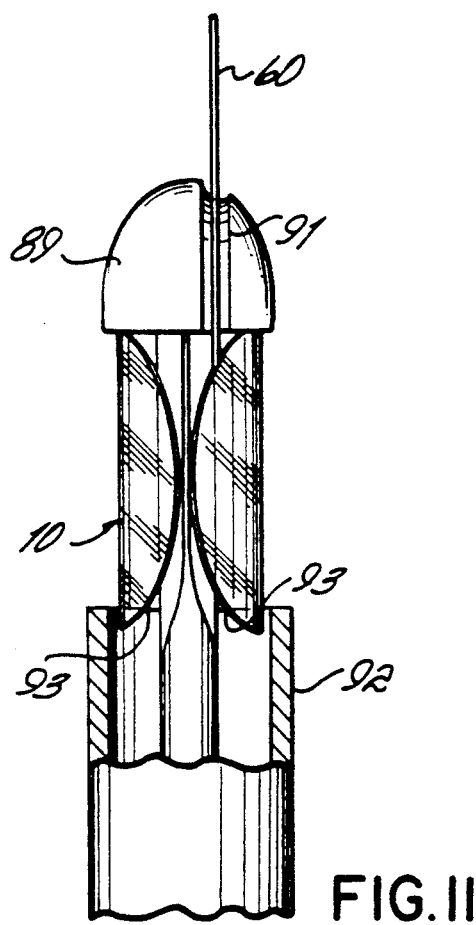
FIG. 11 is an enlarged front elevational view, partly broken away, of the inserter and folded lens shown in FIG. 10.

The thickness of tip 89 approximates that of the folded lens (FIG. 11), and its rounded wedge-like shape helps open the incision for the lens. The tip has a circumferential groove 91, which receives the haptic 60 from the posterior lens leaf 94. When the lens is being folded around the tip, the tip presses against the curve of the haptic, thereby tending to straighten the haptic (to the right in FIG. 11) and reducing its apparent width. This facilitates insertion of the haptic since it does not project so far beyond the width of the folded lens (FIG. 11).

A plastic non-stick sleeve 92 is slidable lengthwise on the inserter to expose or screen the fin 84 and tube end 88. When pushed all the way up (FIG. 9) sleeve 92 covers the blade almost completely so as to protect the blade from bending or damage during storage and cleaning. When pulled partway back, to expose the blade but not tube 86, the tube is insulated from the eye and does not stick to ocular tissues during insertion of the instrument into the eye. The sleeve can be positioned to abut the trailing edge 93 of the lens folded about the blade (FIG. 10), in which position the sleeve helps to push the folded lens into the eye by blocking it from sliding back along tube 86 as the instrument is inserted.

Referring again to FIG. 5, the seat 68 of carrier 76 is shaped to receive the fin blade 84 and tube 86 of inserter 82. The seat 68 has grooves 94 for the haptics. In order to more positively confine and align blade 84 on seat 68, tip 89 is received in and aligned by the upstanding guide 96 on base 66.

To fold a lens seated on seat 68, the tip of one's finger is inserted in the finger recess 98 and arm 72 is lifted and moved clockwise (in the direction of arrow 100 in FIG. 5). Abutment or holding means 102 above seat 68 holds the lens from being shifted off the seat (i.e., to the right in FIG. 5) during folding.

Figure 6:
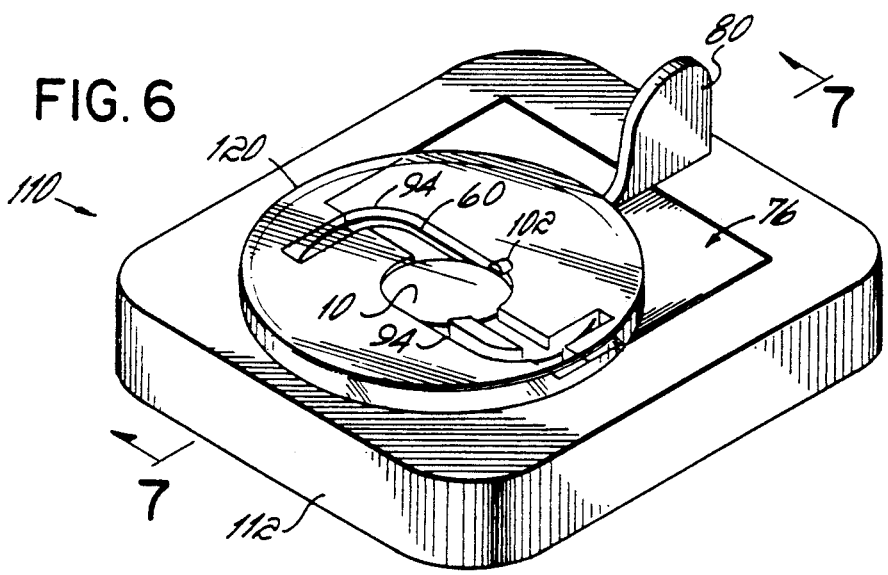
FIG. 6 is a perspective view of a lens package in accordance with the invention and including a lens carrier which is cooperable with the folding apparatus of FIG. 5.
Figure 7:
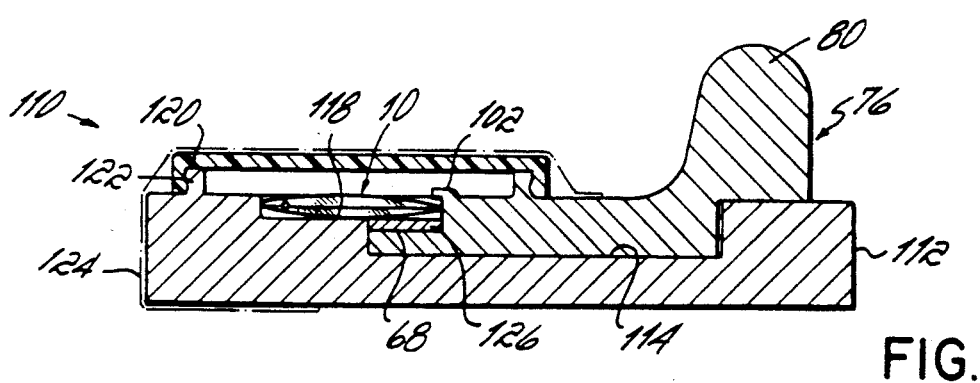
FIG. 7 is a vertical section taken on line 7—7 of FIG. 6, showing the lens within the package.
Figure 8:
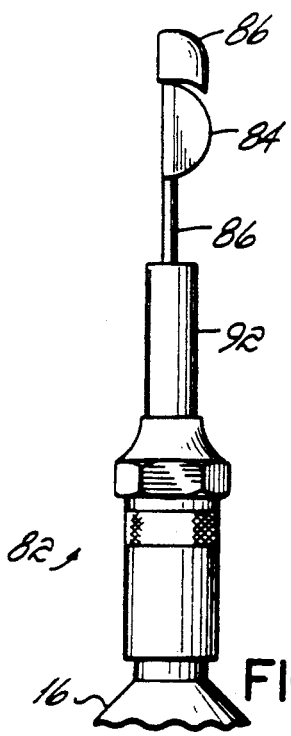
FIG. 8 shows a second form of inserter, having an internally cooled blade and a protective tip, showing the covering sleeve in retracted position.
Figure 9:
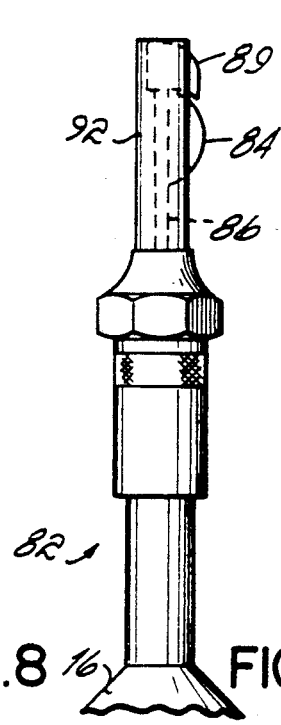
FIG. 9 is a view similar to FIG. 8 but shows the sleeve in fully extended position to cover the blade.

The seat-presenting carrier 76 preferably comprises part of a lens package 110, which is shown in FIGS. 6 and 7. The package includes an outer frame or body 112 having a central recess 114 sized to receive carrier 76. As best shown in FIG. 7, a lens 10 sits on seat 68 with only about half of its width actually supported on the carrier seat, with its other half projecting from seat 68 and supported on a seat 118 in body 112. Holding means 102 holds the lens on seat 68 when the carrier is lifted from its frame 112; and it holds the lens from shifting off its seat while being folded. The lens is enclosed in the package by a removable cup-like cover 120 which snaps onto an upstanding annular rib 122 that is presented in part by frame 112 and in remaining part by carrier 76. The lens can be sterilized in the carrier at the point of manufacture, and sterility is maintained by a protective outer wrap 124 shown in phantom in FIG. 7. At time of use, the outer wrap 124 is removed, carrier 76 is lifted by grip 80 from the frame and is placed into its aperture 78 in the folder base 66, which positions the lens for folding. The lens itself need not be touched at any time during the folding, rigidification, and implanting procedure.

As mentioned above, it is desirable to use carriers which will accommodate lenses of a variety different sizes and shapes. For that purpose an appropriate one of a series of different wafers, shims, or adaptors, one of which is designated 126, can be placed on the seat 68 of the carrier (see FIG. 7) to establish an optimal depth of the surface on which the lens rests so that when the swing arm 72 is rotated to fold the lens, the lens will be closely engaged with the blade for good heat transfer and minimum thickness.

Thus a universal outer frame or body 112 is used with different carriers to accommodate different sizes and shapes of lenses; and different adaptors 126, when placed on the carrier seat 68, will accommodate different powers and thicknesses of lenses. Each lens of a specific power may be used with a corresponding lens adaptor. The thickness of the lens and its adaptor "fills" the lens chamber, when the lens is closed around the blade, to establish the close engagement of the lens on the blade.

Having described the invention, what is claimed is:

1. Apparatus for folding an intraocular lens around a blade of an inserter, comprising,
a base;
said base presenting, a lens seat for supporting a first face of said lens, means for holding a lens on said seat for folding, and positioning means for positioning a lens inserter so that said blade of said inserter is in a desired alignment on a second face of said lens; and
an arm movably attached to said base for folding said lens around said blade of said inserter.

2. The apparatus of claim 1 further including means for supplying a cryogenic fluid around said lens seat to rigidify a lens on said seat in folded configuration around said blade.

3. The apparatus of claim 2 wherein said supply means includes a gas passage for delivering a gas into a cavity around said seat.

4. The apparatus of claim 2 further including valve means for controlling the rate of flow of said cryogenic fluid.

5. The apparatus of claim 1 wherein said seat is adapted to support said lens horizontally.

6. The apparatus of claim 1 wherein said positioning means is a socket in said base, said socket being configured to receive a handle of a lens inserter.

7. The apparatus of claim 6 wherein said arm is pivoted to said base for swinging movement about a hinge axis, and said socket has a longitudinal axis which is parallel to said hinge axis.

8. The apparatus of claim 1 wherein said seat is configured to support a first portion of the width of a lens, the remaining portion of the width of said lens extending off said set in position for engagement by said arm for folding back toward said first portion.

9. The apparatus of claim 8 wherein said arm has a seat portion for engaging said remaining width of said lens.

10. The apparatus of claim 1 wherein said seat is configured to accept the haptics of a lens.

11. The apparatus of claim 1 wherein said arm is movable about an axis parallel to an edge of said seat.

12. The apparatus of claim 1 wherein said arm is adapted to turn about an axis parallel to and laterally offset from the blade of said inserter.

13. The apparatus of claim 1 wherein said holding means includes abutment means adjacent said seat to arrest movement of said lens off said seat during folding.

14. The apparatus of claim 1 wherein said apparatus has a guide for receiving and holding a tip of said inserter in desired alignment on said second face of said lens.

15. The apparatus of claim 14 wherein said seat lies between said positioning means and said guide.

16. The apparatus of claim 1 further wherein said seat is removable from said base, whereby different seats can be inserted in said base to accommodate different shapes and sizes of lenses for folding by said apparatus.

17. Apparatus for folding an intraocular lens about an inserter, comprising,
a base,
a removable lens carrier positionable on said base, said carrier having a seat on which a portion of a first face of the lens can be placed,
positioning means on said base for receiving and holding a lens inserter so that a portion of said inserter is positioned on a second face of said lens for folding said lens on said inserter,
said base having a movable arm for folding said lens around said portion of said inserter,
said base being adapted to selectively receive any of a series of carriers having seats of different configurations so that said folding apparatus can fold lenses of different configurations.

18. The apparatus of claim 17 wherein said seat of said carrier is configured to engage only a portion of said first face of said lens, the remaining portion of said first face of the lens extending off the seat,
said arm having a surface which engages the remaining portion of said first face of said lens for folding.

19. The apparatus of claim 17 wherein said carrier is received in a recess in said base.

20. The apparatus of claim 19 wherein said carrier fits within said recess in said base and said arm is movable over said carrier.

21. The apparatus of claim 17 wherein said carrier has a grip by which it can be removed from said base.

22. The apparatus of claim 17 wherein said seat in said carrier includes a recess for receiving a portion of a haptic projecting from said lens.

23. An unfolded, foldable lens in a carrier therefor, comprising,
a lens carrier having a lens seat adjacent an outer edge of said carrier,
said seat having a lens support surface,
a first portion of one face of said lens resting on said surface, said surface supporting said lens so that the remaining portion of said one face of said lens extends outwardly from said sat and beyond said outer edge of said carrier, said extending portion being engageable for lifting and folding back above the first lens portion while said first portion is resting on said support surface in said carrier, and a removable lens thickness adapter between said first portion of said lens and said seat, said adapter supporting said lens at a desired depth for folding, according to the thickness and power of said lens, and means for holding said first portion of said lens on said support surface when said remaining portion of said lens is being folded back over said first portion.

24. The foldable lens and carrier of claim 23 wherein said carrier further includes means for holding said first portion of said lens on said support surface when said other portion of said lens is being folded back over said first portion.

25. The foldable lens and carrier of claim 23 wherein said seat is a recess in said carrier and said first portion of said one face of said lens is about one-half the width of said lens.

26. The foldable lens and carrier of claim 23 wherein said seat includes a slot for receiving a haptic of said lens.

27. A foldable lens in a carrier therefor, comprising,
a lens carrier body having a seat,
said seat engaging a first portion of said lens,
another portion of said lens projecting outwardly from said carrier, said projecting portion being engageable for folding while said lens is in said carrier, and
a removable lens thickness adapter between said first portion of said lens and said seat,
said adapter supporting said lens at a desired depth for folding, according to the thickness and power of said lens, and means for holding said portion of said lens on said support surface when said another portion of said lens is being folded back over said portion of said lens.

28. The lens and carrier of claim 27 wherein said carrier has gripping means projecting from said body.

29. A package containing an unfolded, foldable intraocular lens, said package comprising,
a frame, a lens carrier removable received in said frame, a lens supported partly by said carrier and partly by said frame, and a removable cover,
said frame having a recess in which said carrier is received,
said carrier having a carrier seat which presents a first lens support surface which engages a first portion of a first face of said lens,
said frame having a frame seat which is adjacent said carrier seat and which presents a second lens support surface that engages a further portion of said first face of said lens,
said cover protectively enclosing said lens,
said first portion of said lens being retained on said carrier seat when said carrier is removed from said frame, said further portion of said lens being engageable while on said carrier seat for folding back over said first portion of said lens.

30. The package of claim 29 wherein said carrier includes means for retaining said lens on said carrier seat.

31. The package of claim 30 wherein said means for retaining said lens on said carrier seat is a tab extending from said carrier, above said carrier seat.

32. The package of claim 29 wherein said cover is secured partially to said frame and in remaining part to said carrier.

33. The package of claim 31 wherein said cover snaps onto an upstanding rib presented in part on said carrier and in part on said frame.

34. The package of claim 29 wherein said carrier has gripping means whereby it may be removed from said frame.

35. The package of claim 29 wherein said carrier includes a lens thickness adapter between said first portion of said lens and said carrier seat, said adapter supporting said lens on said seat at a desired depth for folding, according to the thickness and power of said lens.

* * * * *